US009664643B2

(12) United States Patent
Van Der Voorn et al.

(10) Patent No.: US 9,664,643 B2
(45) Date of Patent: May 30, 2017

(54) CHARACTERIZATION OF PARTICLES

(75) Inventors: Johannes Adrianus Van Der Voorn, Christchurch (NZ); Robert Vogel, Christchurch (NZ); Benjamin Mark Glossop, Christchurch (NZ)

(73) Assignee: IZON SCIENCE LIMITED, Christchurch (NZ)

( * ) Notice: Subject to any disclaimer, the term of this patent is extended or adjusted under 35 U.S.C. 154(b) by 556 days.

(21) Appl. No.: 14/235,989

(22) PCT Filed: Aug. 2, 2012

(86) PCT No.: PCT/EP2012/065191
§ 371 (c)(1),
(2), (4) Date: May 30, 2014

(87) PCT Pub. No.: WO2013/017671
PCT Pub. Date: Feb. 7, 2013

(65) Prior Publication Data
US 2014/0251825 A1 Sep. 11, 2014

(30) Foreign Application Priority Data

Aug. 2, 2011 (GB) .................................. 1113309.7
Mar. 16, 2012 (GB) .................................. 1204693.4

(51) Int. Cl.
*G01N 27/416* (2006.01)
*G01N 33/543* (2006.01)
(Continued)

(52) U.S. Cl.
CPC ......... *G01N 27/4161* (2013.01); *G01N 15/12* (2013.01); *G01N 27/48* (2013.01);
(Continued)

(58) Field of Classification Search
CPC ............... G01N 27/4161; G01N 27/48; G01N 33/48721; G01N 15/12; G01N 33/54313; G01N 2015/0038; G01N 2015/1075
See application file for complete search history.

(56) References Cited

U.S. PATENT DOCUMENTS 3,815,022 A 6/1974 Golibersuch
7,077,939 B1 7/2006 Crooks et al.
(Continued)

FOREIGN PATENT DOCUMENTS

CN 101772697 A 7/2010
GB 2 421 303 A 6/2006
(Continued)

OTHER PUBLICATIONS

Chinese Office Action dated Apr. 1, 2015 for corresponding Chinese Application No. 201280048595.7.
(Continued)

*Primary Examiner* — Sean E Conley
*Assistant Examiner* — Matthew Krcha
(74) *Attorney, Agent, or Firm* — Renner, Otto, Boisselle & Sklar, LLP

(57) ABSTRACT

A method of determining the charge of at least one test particle, comprising: applying one of an electric current or a voltage across an aperture connecting two chambers, whereby the chambers are at least partially filled with electrolyte and whereby the at least one test particle is suspended in the electrolyte of at least one of the chambers; measuring the other of the electric current or voltage across the aperture; varying a pressure differential between the two chambers; and determining the charge based on the measurements of the electric current or voltage.

8 Claims, 11 Drawing Sheets

(51) Int. Cl.
  *G01N 15/12*    (2006.01)
  *G01N 27/48*    (2006.01)
  *G01N 33/487*   (2006.01)
  *G01N 15/10*    (2006.01)
  *G01N 15/00*    (2006.01)

(52) U.S. Cl.
  CPC . *G01N 33/48721* (2013.01); *G01N 33/54313* (2013.01); *G01N 2015/0038* (2013.01); *G01N 2015/1075* (2013.01)

(56) References Cited

U.S. PATENT DOCUMENTS

| | | | |
|---|---|---|---|
| 7,288,219 B1 | 10/2007 | Roos | |
| 2002/0127855 A1* | 9/2002 | Sauer | C12Q 1/6825 438/689 |
| 2004/0236521 A1 | 11/2004 | Dukhin | |
| 2007/0190543 A1* | 8/2007 | Livak | C12Q 1/6816 435/6.19 |
| 2013/0176563 A1* | 7/2013 | Ozawa | B82Y 5/00 356/301 |

FOREIGN PATENT DOCUMENTS

| | | | | |
|---|---|---|---|---|
| GB | 2 477 287 A | 8/2011 | | |
| GB | 2 477 663 A | 8/2011 | | |
| JP | WO 2012043028 A1 * | 4/2012 | | B82Y 5/00 |
| WO | WO 01/81896 A1 | 11/2001 | | |
| WO | WO 2004/028673 A1 | 4/2004 | | |
| WO | WO 2006/063872 | 6/2006 | | |
| WO | WO 2008/051308 A2 | 5/2008 | | |

OTHER PUBLICATIONS

European Office Action dated Jul. 2, 2015 for corresponding European Application No. 12 753 408.9.
Chinese Office Action dated Feb. 14, 2016 for corresponding Chinese Application No. 201280048595.7.
International Search Report and Written Opinion for corresponding International Application No. PCT/EP2012/065191 mailed Jan. 3, 2013.
British Search Report for correspondence British Application No. GB1204693.4 dated Apr. 25, 2012.

* cited by examiner

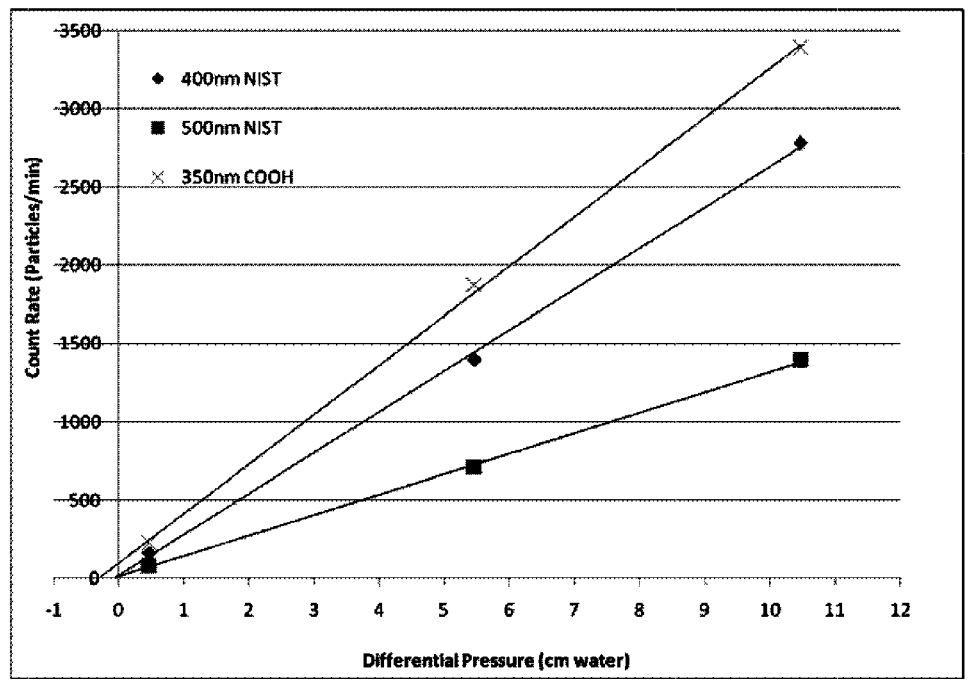
Fig. 3a
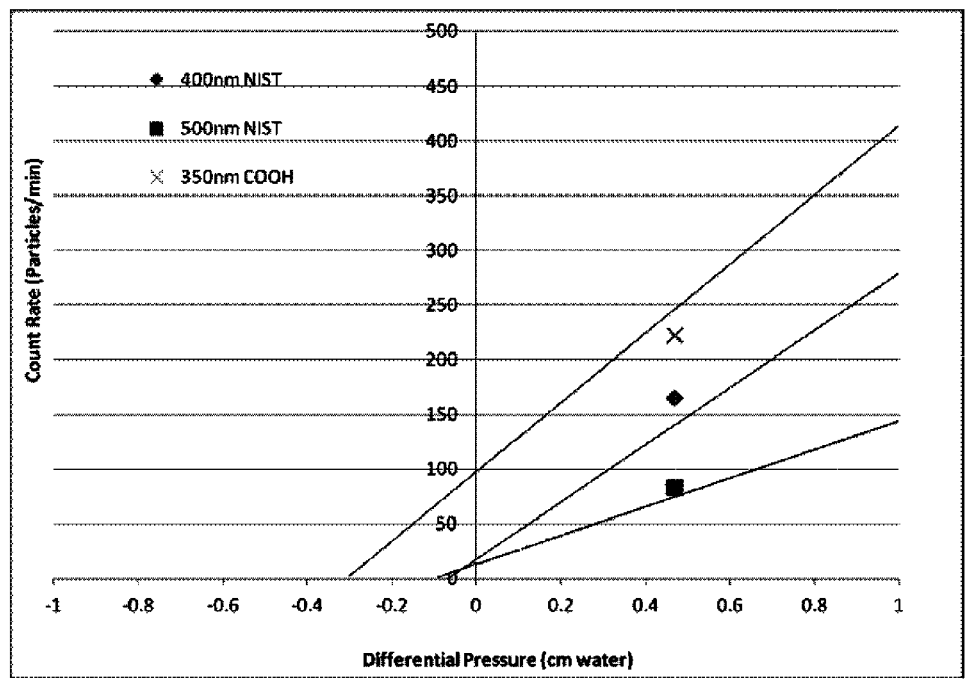
Fig. 3b – Zoomed in to X Axis Intercept

CHARACTERIZATION OF PARTICLES

The present invention relates to the characterisation of particles and to particle-sensitive or radiation-sensitive devices and associated methods. Examples of such a device and associated method are disclosed in WO 2006/063872, which is hereby incorporated by reference for all purposes. It is an aim of at least one aspect of the present invention to develop such devices and methods further, but it should be noted that the present invention and its applications are not limited to devices and methods of the type disclosed in WO 2006/063872.

According to a first aspect of the invention, there is provided a method of determining the charge of at least one test particle, comprising:
- applying one of an electric current or a voltage across an aperture connecting two chambers, whereby the chambers are at least partially filled with electrolyte and whereby the at least one test particle is suspended in the electrolyte of at least one of the chambers;
- measuring the other of the electric current or voltage across the aperture;
- varying a pressure differential between the two chambers; and
- determining the charge based on the measurements of the electric current or voltage.

According to a further aspect of the invention, there is provided a method of determining the direction in which a test particle travels through an aperture connecting two chambers, whereby the chambers are at least partially filled with electrolyte and whereby the test particle is suspended in the electrolyte, the method comprising:
- applying one of an electric current or a voltage across the aperture;
- monitoring the other of the electric current or voltage across the aperture; and
- relating an asymmetry of the monitored electric current or voltage to an asymmetry of the aperture.

According to a further aspect of the invention, there is provided a method of determining the velocity with which a test particle travels through an aperture connecting two chambers, whereby the chambers are at least partially filled with electrolyte and whereby the test particle is suspended in the electrolyte, the method comprising:
- applying one of an electric current or a voltage across the aperture;
- monitoring the other of the electric current or voltage across the aperture; and
- determining said velocity based on a result of said monitoring.

According to a further aspect of the invention, there is provided a method of determining the charge of at least one test particle, comprising:
- applying one of an electric current or a voltage across an aperture connecting two chambers, whereby the chambers are at least partially filled with electrolyte and whereby the at least one test particle is suspended in the electrolyte of at least one of the chambers;
- monitoring the other of the electric current or voltage across the aperture so as to monitor at least one blockade event, the blockade event being represented by a variation in the monitored electric current or voltage as the at least one test particle travels through the aperture thereby varying the electric current or voltage; and
- determining the charge based on a value indicative of the duration of a blockade event or a rate of change of the monitored electric current or voltage.

According to a further aspect of the invention, there is provided a method comprising:
- applying one of an electric current or a voltage across an aperture connecting two chambers, whereby the chambers are at least partially filled with electrolyte and whereby a plurality of test particles are suspended in the electrolyte of at least one of the chambers;
- measuring the other of the electric current or voltage across the aperture;
- varying a pressure differential between the two chambers; and
- monitoring a change in the measured electric current or voltage, said change being indicative of a variation of the number or concentration of test particles in the aperture; and
- determining that a pressure differential between the two chambers is substantially zero when said change occurs.

According to a further aspect of the invention, there is provided a method comprising:
- applying one of an electric current or a voltage across an aperture connecting two chambers, whereby the chambers are at least partially filled with electrolyte and whereby a plurality of test particles are suspended in the electrolyte of at least one of the chambers;
- monitoring the other of the electric current or voltage across the aperture so as to monitor a plurality of blockade events, the blockade events being represented by a variation in the monitored electric current or voltage as the test particles travel through the aperture thereby varying the electric current or voltage;
- monitoring a characteristic of at least two blockade events; and
- deriving information indicative of a distribution or variation of a feature of the particles based on the monitored characteristic.

According to a further aspect of the invention, there is provided a method for determining the charges of different particle types in a mixed sample comprising:
- applying one of an electric current or a voltage across an aperture connecting two chambers, whereby the chambers are at least partially filled with electrolyte and whereby a plurality of test particles are suspended in the electrolyte of one of the chambers;
- applying a pressure differential between the two chambers to drive the test particles away from the aperture;
- thereafter reducing, or setting to zero, the pressure differential such that the particles return to the aperture under electrophoresis, and
- determining the rate at which the test particles return to the aperture and translocate through the aperture as an indication of relative charge.

According to a further aspect of the invention, there is provided a system comprising:
- a first chamber arranged to be exposed to a first pressure;
- a second chamber connected to a first end of a conduit, wherein a second end of the conduit is arranged to be at least partially suspended in a fluid;
- wherein the first and second chambers are connected by an aperture; and
- wherein the pressure in the second chamber is arranged to be varied by varying the amount by which the second end of the conduit is suspended in a fluid.

According to a further aspect of the invention, there is provided a method comprising:
- applying one of a voltage or an electric current across an aperture connecting two chambers, whereby the chambers are at least partially filled with electrolyte and whereby a plurality of test particles are suspended in the electrolyte of at least one of the chambers;
- measuring the other of the voltage or electric current through the aperture;
- varying a pressure differential between the two chambers and/or voltage or current through the aperture; and
- determining when a driving force on the test particles due to a pressure differential between the two chambers is substantially balanced by a driving force on the test particles due to said voltage.

According to a further aspect of the invention, there is provided an apparatus for determining the charge of at least one test particle, comprising:
- a first chamber and a second chamber, whereby first and second chambers are connected by an aperture;
- means for applying an electric current or a voltage across the aperture;
- means for measuring the other of the electric current and voltage across the aperture when the chambers are at least partially filled with electrolyte and when the at least one test particle is suspended in the electrolyte of at least one of the chambers;
- means for varying the pressure differential between the first and second chambers; and
- means for determining the charge based on the measurements of the electric current and/or voltage.

According to a further aspect of the invention, there is provided an apparatus for determining the direction in which a test particle travels through an aperture, comprising:
- a first chamber and a second chamber, whereby the first and second chambers are connected by the aperture;
- means for applying one of an electric current or a voltage across the aperture;
- means for monitoring the other of the electric current or voltage across the aperture when the chambers are at least partially filled with electrolyte and when the test particle is suspended in the electrolyte; and
- means for relating an asymmetry of the monitored electric current or voltage to an asymmetry of the aperture.

According to a further aspect of the invention, there is provided an apparatus for determining the velocity with which a test particle travels through an aperture, comprising:
- a first chamber and a second chamber, whereby the first and second chambers are connected by the aperture;
- means for applying one of an electric current or a voltage across the aperture;
- means for monitoring the other of the electric current or voltage across the aperture when the chambers are at least partially filled with electrolyte and when the test particle is suspended in the electrolyte; and
- means for determining said velocity based on a result of said monitoring.

According to a further aspect of the invention, there is provided an apparatus for determining the charge of at least one particle, comprising:
- a first chamber and a second chamber, whereby the first and second chambers are connected by an aperture;
- means for applying one of an electric current or a voltage across an aperture;
- means for monitoring the other of the electric current or voltage across the aperture when the chambers are at least partially filled with electrolyte and when the at least one test particle is suspended in the electrolyte of at least one of the chambers, so as to monitor at least one blockade event, the blockade event being represented by a variation in the monitored electric current or voltage as the at least one test particle travels through the aperture thereby varying the electric current or voltage; and
- means for determining the charge based on a value indicative of the duration of a blockade event or a rate of change of the monitored electric current or voltage.

According to a further aspect of the invention, there is provided an apparatus comprising;
- a first chamber and a second chamber, whereby the first and second chambers are connected by an aperture;
- means for applying one of an electric current or a voltage across the aperture;
- means for measuring the other of the electric current or voltage across the aperture when the chambers are at least partially filled with electrolyte and when a plurality of test particles are suspended in the electrolyte of at least one of the chambers;
- means for varying a pressure differential between the two chambers; and
- means for monitoring a change in the measured electric current or voltage, said change being indicative of a variation of the number or concentration of test particles in the aperture; and
- means for determining that a pressure differential between the two chambers is substantially zero when said change occurs.

According to a further aspect of the invention, there is provided an apparatus comprising;
- a first chamber and a second chamber, whereby first and second chambers are connected by an aperture;
- means for applying one of an electric current or a voltage across the aperture;
- means for monitoring the other of the electric current or voltage across the aperture when the chambers are at least partially filled with electrolyte and when a plurality of test particles are suspended in the electrolyte of at least one of the chambers, so as to monitor a plurality of blockade events, the blockade events being represented by a variation in the monitored electric current or voltage as the test particles travel through the aperture thereby varying the electric current or voltage;
- means for monitoring a characteristic of at least two blockade events; and
- means for deriving information indicative of a distribution or variation of a feature of the particles based on the monitored characteristic.

According to a further aspect of the invention, there is provided an apparatus for determining the charges of different particle types in a mixed sample, comprising:
- a first chamber and a second chamber, whereby the first and second chambers are connected by an aperture;
- means for applying one of an electric current or a voltage across the aperture when the chambers are at least partially filled with electrolyte and when a plurality of test particles are suspended in the electrolyte of one of the chambers;
- means for applying a pressure differential between the two chambers to drive the test particles away from the aperture;
- means for thereafter reducing, or setting to zero, the pressure differential such that the particles return to the aperture under electrophoresis, and means for determining the rate at which the test particles return to the aperture and translocate through the aperture as an indication of relative charge.

According to a further aspect of the invention, there is provided an apparatus comprising:

a first chamber and a second chamber, whereby the chambers are connected by an aperture;

means for applying one of a voltage or an electric current across the aperture;

means for measuring the other of the voltage or electric current through the aperture when the chambers are at least partially filled with electrolyte and when a plurality of test particles are suspended in the electrolyte of at least one of the chambers;

means for varying a pressure differential between the two chambers and/or voltage or current through the aperture; and means for determining when a driving force on the test particles due to a pressure differential between the two chambers is substantially balanced by a driving force on the test particles due to said voltage.

Some embodiments of the invention will now be described by way of example only and with reference to the accompanying drawings, in which:

FIG. 3a is a graph showing differential pressure on the horizontal axis and count rate on the vertical axis;

FIG. 3b is a graph showing differential pressure on the horizontal axis and count rate on the vertical axis;

Figure 1:
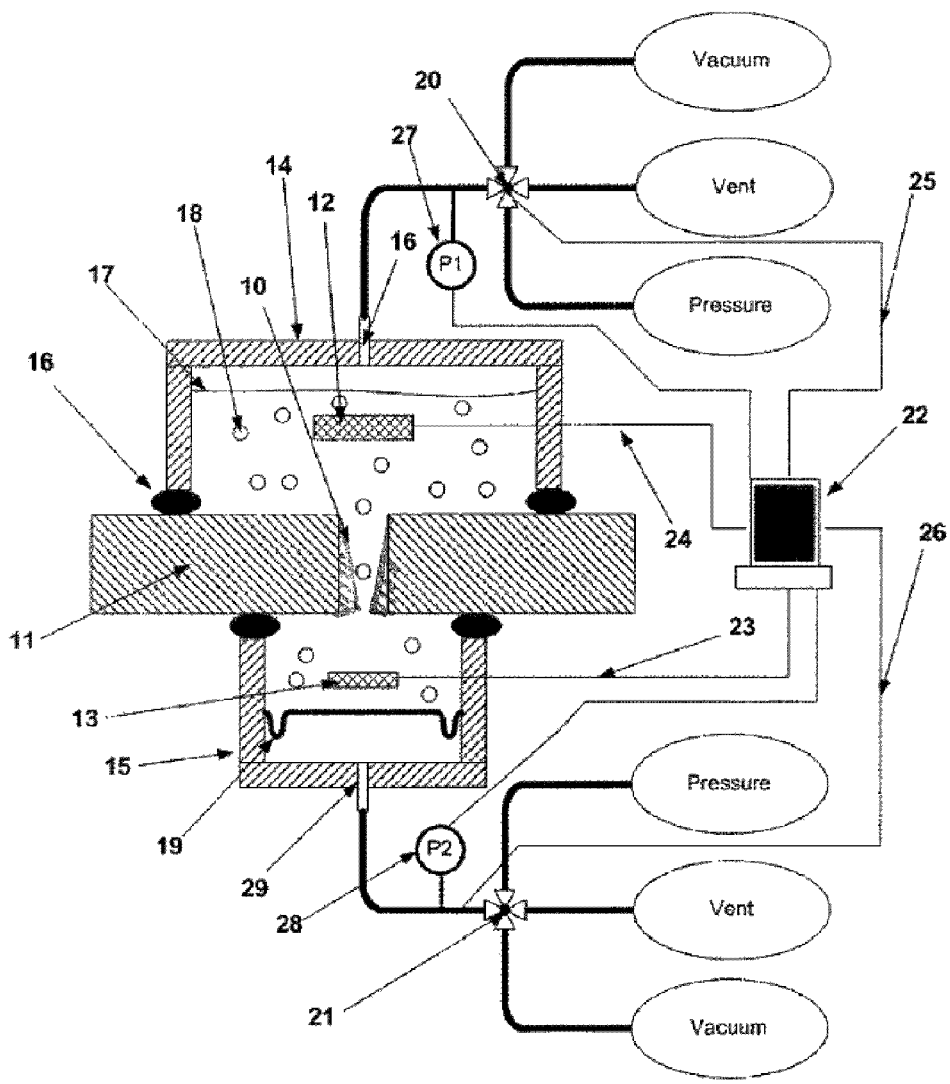
FIG. 1 is a schematic of an apparatus for electrophoresis measurements.

FIG. 1 shows an exemplary apparatus for electrophoresis measurements. The apparatus has two chambers 14, 15, both at least partially filled with an electrolyte, which is a fluid containing dissolved ions. The two chambers are separated by a membrane 11. The membrane defines a pore 10 (or aperture), through which electrolyte can move from one chamber to the other chamber. The pressure difference across the membrane can be controlled.

An electrode 12, 13 is provided in each chamber 14, 15 such that a voltage difference between the two chambers may be controlled. The voltage difference creates an electric current in the electrolyte from one electrode to the other electrode. This current may be measured by a current meter. Alternatively, the current may be controlled and the voltage may be measured by a volt meter.

Particles 18 may be suspended in the electrolyte of one or both of the chambers and the apparatus may be used to characterise properties of those particles. The concentration of particles may be the same in each chamber or may be different. The apparatus may be suitable to measure the charge, size, concentration, shape, flexibility, diffusion, dispersion or aggregation of the particles.

The pore may be flexible and may be adapted in shape during measurements or between measurements, or the pore may be rigid and fixed in size and shape. The size of the pore is normally bigger than the size of the particles, but is typically of the same order of magnitude as the size of the particles.

The particles may be driven through the pore by the pressure differential and/or the voltage differential between the chambers and across the pore. When a particle passes through the pore, at least some part of the electric current through the electrolyte is temporarily blocked by the particle. The blockade event will be recorded by the electric current meter as a temporary decrease of the electric current.

As used in the present specification, the term "blockade event", "blockade" or "event" may refer to the presence of a particle in or near the pore and therefore the blocking of (a portion of) current through the pore, or it may refer to a recording or visualisation of measurements (most commonly current over time) relating to this. This will be clear from the context. Similarly, the term "width of the blockade" may refer to the width of a visualisation of such measurements (usually current over time).

Figure 2:
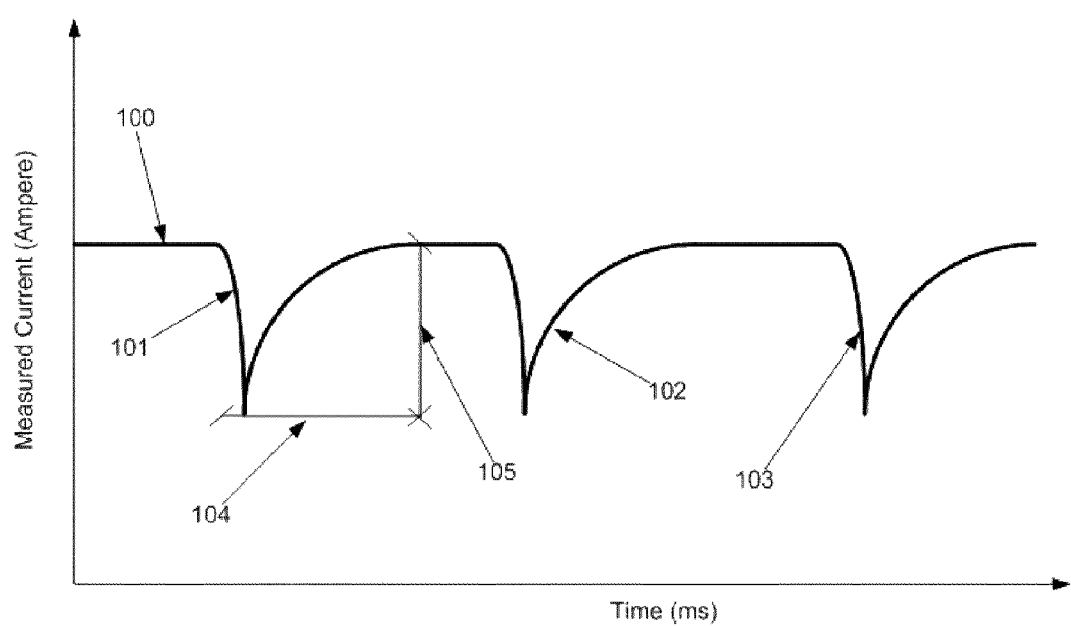
FIG. 2 is a graph showing a measured current on the vertical axis and time on the horizontal axis.

The shape of the pore may be frustoconical. The shape of the blockade measurement of the current versus time will in that case be asymmetrical, because when the particle passes through the narrow part of the cone (towards the tip of the cone) more electric current will be blocked than when the particle passes through the wider part of the cone (towards the base of the cone). An illustration of an electric current measurement of a series of blockade events is shown in FIG. 2. The background signal in FIG. 2 is shown as a flat signal, but in an actual measurement the signal to noise ratio will be finite. As can be seen in FIG. 2, the recorded events are asymmetrical and have one edge which is steeper than the other edge, corresponding to the asymmetrical shape of the pore. The point where the two edges meet is the 'deepest' point where a maximum of the current is blocked for that event, but deepest point does not necessarily correspond to the particle passing through the narrowest part of the pore. If the orientation of the pore is known, the shape of the measured blockade event shows in which direction the particle has traveled through the pore. By way of example, if the pore of the measurements of FIG. 2 was positioned with the narrow part of the pore up and the wide part of the pore down, then the particles moved from the top to the bottom reservoir according to the measurements of FIG. 2.

The transport of particles through the pore may be driven by several mechanisms. A first mechanism is electrophoresis, which is caused by the electromagnetic interaction between the electric field in the electrolyte and a charge of the particle. The dispersed particles have an electric surface charge, which is a charge present at an interface between the particle surface and the surrounding electrolyte, and the electric field exerts an electrostatic Coulomb force on that surface charge. The Coulomb force drives the particle through the electrolyte.

A second mechanism is electro-osmosis. Electro-osmosis in a pore may cause the movement of liquid adjacent to the charged pore wall under the influence of an electric field. For a negatively charged pore surface there will be an excess of positive ions in the adjacent liquid and as the ions move under the electric field they will draw the liquid along with them, resulting in a plug flow and electro-osmotic pressure. Plug flow is a model in fluid mechanics for describing the flow of fluid in a pipe. The electro-osmotic pressure increases with decreasing pore diameter.

A third mechanism is transport by a pressure differential between the two chambers. The pressure may be applied by external controllers and the particles will be driven from the reservoir with a higher pressure to the reservoir with a lower pressure. In a specific embodiment of the apparatus, the orientation of the reservoirs is such that one is located above the other. The electrolyte in the upper reservoir will be driven to the lower reservoir by gravity if no additional pressure is applied to either of the chambers. By way of example, an electrolyte layer of around 5 to 10 mm directly above the pore in the top reservoir is enough to drive the particles through the pore. This pressure due to the weight of the layer of fluid in the top chamber is also called head pressure. A small static head pressure, for example 4.7 mm in the case of a cell currently available from Izon Science Limited, can generate a large flow rate of fluid in a large nanopore. The same applied pressure will cause a very different flow rate in different sized pores. Extremely fine pressure adjustment means may be required to allow charge measurement of 1 micron particles and above.

A fourth mechanism is diffusion of the particles in the electrolyte, but this mechanism typically contributes much less to transport of the particles than the mechanisms discussed above and may therefore be ignored.

The total particle transport through the pore can be summarised using the Nernst-Planck approach:

$$\frac{J}{C} = \epsilon \frac{(\zeta_{particle} - \zeta_{pore})E}{\eta} + \frac{Q_P}{A} \quad (1)$$

where J is the total particle flux, C is particle concentration, $\epsilon$ and $\eta$ are the permittivity and kinematic viscosity of the electrolyte respectively, $\zeta$ indicates the zeta potential, E is the electric field, $Q_P$ is the pressure-driven volumetric flow rate, and A is the cross-sectional area of the pore constriction. The equation includes contributions due to electrophoresis (term including $\zeta_{particle}$), electro-osmosis (term including $\zeta_{pore}$) and hydrodynamic transport (pressure). Diffusion has been omitted because its contribution is negligible compared to the other terms. Electro-osmotic and electrophoretic contributions are estimated using the Smoluchowski equation, which is a well known diffusion equation with drift term. This is a good approximation for a monovalent electrolyte concentration of 0.1 M and particle sizes of approximately 200 nm, where the product of particle radius and inverse Debye-length is much larger than 1.

The zeta potential is the electric potential in the interfacial double layer at the location of the slip plane versus a point in the bulk fluid away from the interface. In other words, zeta potential is the potential difference between the dispersion medium and the stationary layer of fluid attached to the dispersed particle.

Calculation of the zeta potential may be achieved by setting J=0 in equation 1, so that the applied pressure exactly opposes the combined effect of electro-osmosis, electrophoresis and inherent pressure. Use of equation 1 may require measurement of $\zeta_{pore}$, and determination of the inherent pressure head. Of the other terms, $\epsilon$ and $\eta$ are known under standard laboratory conditions, while $Q_P$, A and E can be calculated using a conical profile based on scanning electron microscope imaging of the pore under the same stretch conditions used in the experiments. The pore wall zeta potential can be determined by measuring electro-osmosis in a well-defined channel.

When all other terms in equation 1 are known, the unknown parameter such as the concentration or charge of the particles can be calculated, but in practical applications not all other terms may be known. For example, the diameter of a particular nanopore may not be known. If not all parameters are known, the value of the charge (or other parameters) of a particle may be determined, according to an embodiment of the invention, by calibrating the system with particles with a known charge (or other corresponding parameter).

An example of a graph of the pressure (horizontal axis) versus the rate of blockade events is shown in FIG. 3. In this example, the electric potential and pressure forces are acting in the same direction, so the particles are translocating in one direction only. Three lines are shown, one for an example of a calibration particle (the top line) and two for unknown particles (the two lower lines). As can be seen from the Figure, there is a linear relation between the pressure and the count rate. The lines are drawn through a set of measurements as indicated in the Figure. At the point where the pressure is zero (the vertical axis), the count rate is not zero, because at that point the electric field still causes transport of particles. The lines can be extrapolated to the point where the lines cross the horizontal axis, which point indicates the pressure required to balance out the transport due to the electric field to create substantially zero events.

The point where on average no transport of particles takes place, i.e. where the lines cross the horizontal axis, is where the different forces on a particle cancel each other out. In big pores no transport will normally take place at that balance point, but in smaller pores—typically with the small diameter smaller than a 1 μm—there will still be residual events at the balance point.

This balance point is of particular interest, because the corresponding applied pressure is proportional to the charge, according to empirical evidence.

The horizontal axis of FIG. 3 shows the applied pressure, which is the pressure applied to the upper chamber by a pressure controller. The applied pressure does not include inherent pressure, which is due to the pressure head and meniscus, and electro-osmotic pressures. The meniscus is the curve in the upper surface of the liquid close to the surface of the upper chamber and contributes to the pressure in the pore. The inherent pressure and electro-osmotic pressure have been determined and then subtracted from the value of the applied pressure according to a pressure meter in the top chamber, thereby correcting the applied pressure. After correction, the equation describing the particle flux and providing a model to explain FIG. 3 only contains two terms on the right hand side, the transport due to electrophoresis and the transport due to (corrected) applied pressure.

Depending on the physical layout of the test apparatus, an inherent differential pressure across the nanopore is likely to be present. This could be due to a difference in height of the fluid or a difference in meniscus forces on either side of the nanopore. This inherent pressure should be quantified and accounted for in order to improve the accuracy of charge measurements. The inherent pressure can be determined by using a large micron pore (typically larger than 5 μm) and ideally uncharged particles. In this example the inherent pressure is vastly dominating electrophoresis and electro-osmotic pressure. By first applying a vacuum on the top cell and then varying the pressure, the pressure required to stop particle flow can be determined. At this balance point no particles traverse the pore anymore and the applied pressure is opposing the inherent pressure, thus providing a value for the inherent pressure by reading the value of the applied pressure on the pressure meter in the upper chamber.

Figure 11:
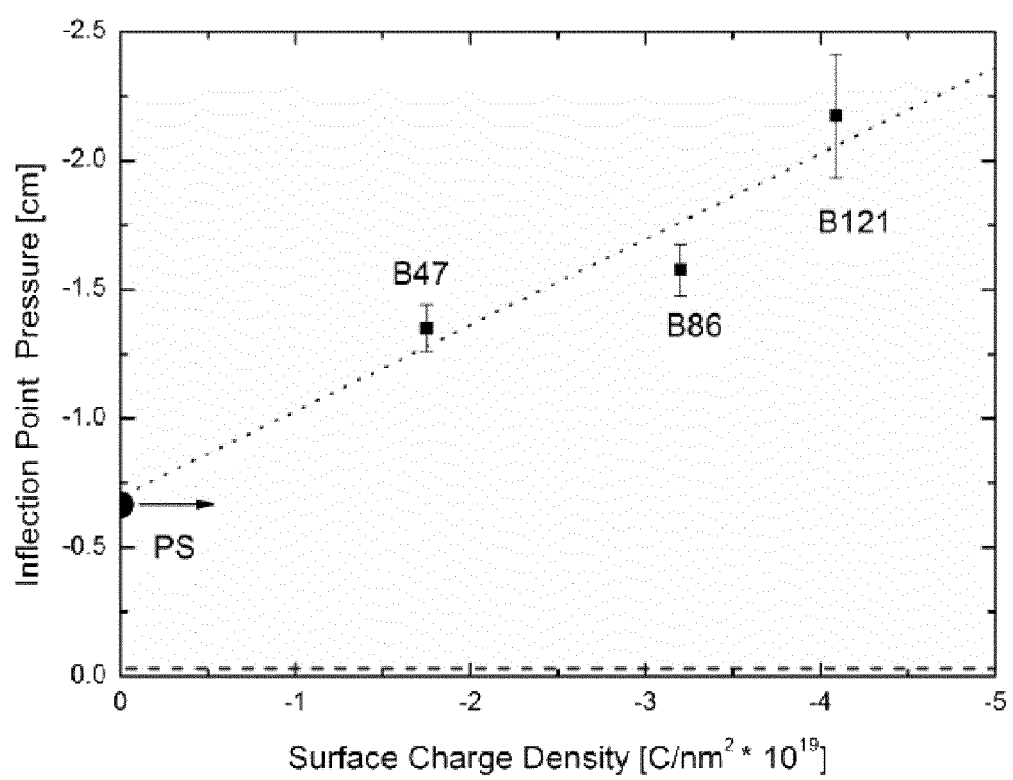
FIG. 11 is a graph showing surface charge density on the horizontal axis and inflection point pressure on the vertical axis.

The electro-osmotic pressure can be determined by plotting the pressures at the balance point for a range of calibration particles (at least 3) versus the surface charge densities of these particles. Carboxylated particles with different functional group (COOH) surface densities may be used as calibration, where the functional group density has been determined by titration. The pressures at the balance point for these 'calibration particles' can be fitted with a linear curve and the electro-osmotic pressure can be extracted from the y-intercept of this curve, as shown in FIG. 11.

After having determined the inherent pressure and the electro-osmotic pressure, the corrected applied pressure is proportional to the charge. In the horizontal axis of the graph of FIG. 3, the inherent pressure head has been added to the externally applied pressure head. The electro-osmotic pressure head has been ignored in this case, due to the large size of the nanopore. In FIG. 3, the horizontal axis shows the corrected applied pressure. The proportionality constant may be determined by using calibration particles. The pressure is equal to a constant times the charge, and if the pressure and charge are known the constant can be calculated. Knowing now the constant, an unknown charge can then be calculated if the pressure is known.

In practice however, it is difficult to accurately determine this 'balance point' experimentally, because the signal is jittery around that point. This is due to some residual events taking place in both directions, including events with very low magnitude, which might be a result of particles accessing the pore sensing zone, but not passing fully through the pore (no-through events). Near the balance point blockade events with more than one peak occur, which suggest that single particles oscillate within the pore instead of passing through the pore without reversing direction of motion. Therefore, it is more accurate to determine the balance point by extrapolating the straight lines to the point where the lines cross the horizontal axis (as per FIG. 3 and described above) than to determine the balance point experimentally.

An example of the calculation of an unknown charge following this method is as follows: As equipment a standard qNano system is used with an NP400 nanopore (200 nm to 800 nm+ sensing range), both available from Izon Science Limited. Potassium Chloride electrolyte of 0.1M and pH8 is used. The calibration particles are 350 nm COOH, which are 350 nm carboxylated polystyrene particles produced by Bangs Laboratories and certified by Izon for size and concentration. These particles have a high negative charge in the KCl buffer. The test particles with unknown charge are NIST400 (400 nm diameter polystyrene particles) and NIST504 (504 nm diameter polystyrene particles). These test particles are not surface-modified with negative functionalities such as carboxyl groups and hence they have a low negative charge in the KCl buffer.

The particles are put into one chamber of the fluid cell and a voltage is applied. A series of increasing pressures are applied that are moving the particles in the same direction as the voltage. The count rate is measured and plotted against the corresponding pressure. Note that in the pressure axis of FIG. 3, the static pressure head (4.7 mm) and the applied pressure have been corrected for.

The charge of unknown particles is calibrated against a particle of known charge. The intercept with the horizontal axis represents the differential pressure required to stop the particles from translocating the pore. The ratio of differential pressures at the intercept for the various samples is proportional to the ratio of electrophoretic mobility and therefore zeta potential. In this application, the terms charge and zeta potential are used interchangeably, but both refer to $\zeta_{particle}$ in the first term on the right hand side of equation 1.

Example data corresponding to the lines shown in FIG. 3 are as follows: the 350 nm COOH test particles have an x-intercept (i.e. pressure at the interception point of the horizontal axis) of −0.30 cm of water and a known charge of −30 mV. The first test particle NIST400 has an x-intercept at −0.06 cm of water and it follows that it has a charge of −6 mV. The second test particle NIST504 has an x-intercept of −0.10 cm of water and consequently a charge of −10 mV.

Figure 4:
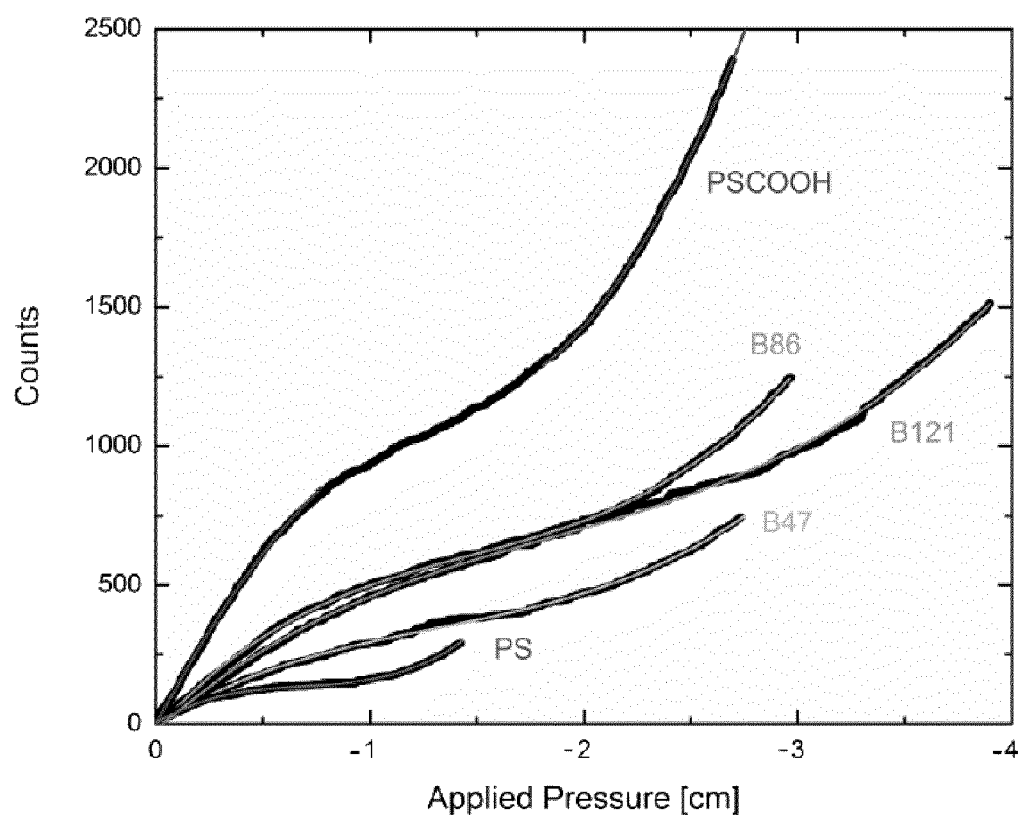
FIG. 4 is a graph showing applied pressure on the horizontal axis and counts on the vertical axis.

An embodiment of the method to determine the balance point other than by determining the x-intercept is by tuning the pressure in a continuous manner and recording the total number of events as a function of time. A graph of the accumulated number of events versus time for several types of particles is shown in FIG. 4. All events are counted (as positives), regardless of the direction of translocation. Starting with a flow of particles in one direction (extreme left of FIG. 4), the pressure is increased and passes through the balance point, where the graph goes through an inflection point due to a large reduction in the frequency of events, and after increasing the pressure more the particles will start moving in the opposite direction through the pore and the number of accumulated particles is increasing again. In other words, the accumulative counts versus applied pressure describe an S-curve.

The next step after recording the graph of FIG. 4 is fitting the two branches of the S-curve with parabolas, and then determining the value of the pressure corresponding to the balance point, which is the point on the graph where the slope is at its minimum. Other fitting functions could also be used and it would also be possible to fit only one branch of the S-curve. From empirical evidence this method is shown to be a very accurate way of determining the 'balance' point where the transport due to a pressure differential balances out the transport due to electric field differential. After calibrating with known particles (as explained above), the charge can now be determined. The curve in FIG. 4 is point symmetric and can be fitted sufficiently accurately with two parabolic curves on both sides of the balance point. We note that in close vicinity (several mm $H_2O$) of the balance point the experimental curve cannot be fitted by a parabolic curve due to multi-peak and no-through events, as described above. Therefore, the fits are made in a region not extending to the balance point or through the balance point. After the fits have been made, the balance point can be determined by extrapolation of the fitting results. The method of fitting a curve through the measurements is described in more detail further below.

The concentration of particles in the upper and lower chambers should be approximately equal, otherwise the count rate for particles moving up through the pore will be different from the count rate for particles moving down through the pore.

Figure 5:
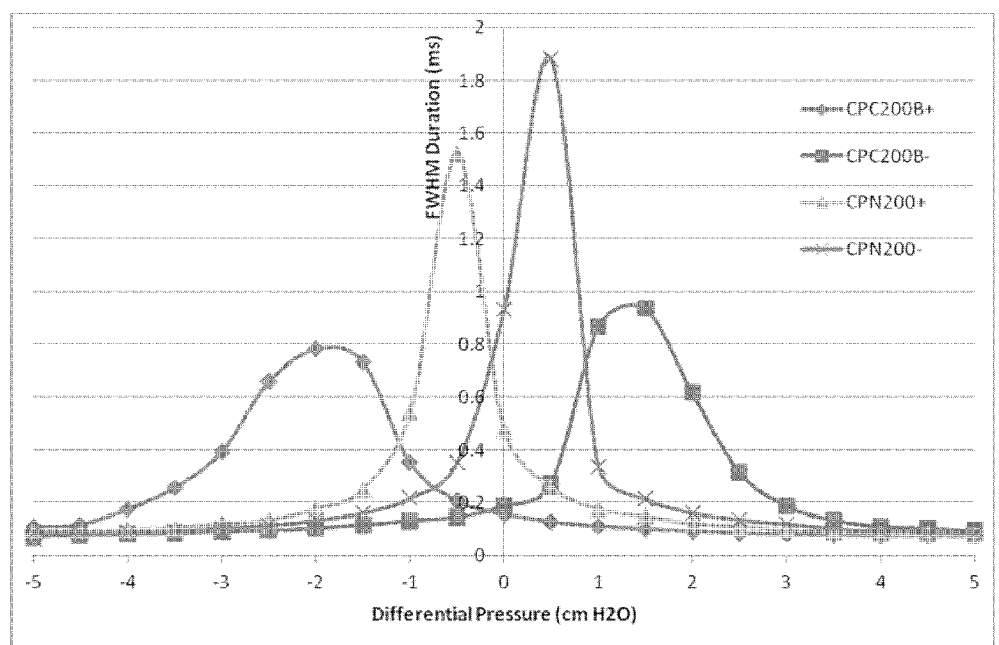
FIG. 5 is a graph showing differential pressure on the horizontal axis and the width of a blockade event on the vertical axis.

Yet a different embodiment of the method for determining this balance point is illustrated in FIG. 5. The pressure gradient across the nanopore is varied in a continuous manner from a positive applied pressure to a negative applied pressure. The time (full width at half max of the electric current blockade event) it takes for each individual particle to translocate the nanopore is measured and averaged for each applied pressure. A maximum duration indicates that pressure and electrophoretic forces are balanced—i.e. the speed at which individual particles translocate the nanopore is at its slowest. In this example the "Full Width Half Max" duration is used—this produces a comparative duration measurement that is independent of particle size. This is also an accurate method for determining the balance point.

In the specific example shown in FIG. 5, the corrected pressure is varied from +5 cm water to −5 cm water in 0.5 cm steps as before. The equipment is a standard qNano system with a NP200 nanopore (100 nm to 400 nm+ sensing range), available from Izon Science Limited, and Potassium Chloride electrolyte (0.1M pH8). The calibration particles with known charge are CPC200B, which are 200 nm diameter carboxylated polystyrene particles produced by Bangs Laboratories. These particles have a high negative charge in the KCl buffer. The particles of unknown charge are CPN200A, which are 200 nm polystyrene particles. These particles are expected to have a very low negative charge in the KCl buffer.

In the example of FIG. 5, the static pressure head (4.7 mm) and the applied pressure have been accounted for; the pressure sweep has been undertaken in distinct 5 mm $H_2O$ pressure steps as opposed to a continuous change; the pressure sweep has been done at both a positive and negative voltage for each sample (denoted by a + or − after the particle description in FIG. 5 and Table 1). This gives an approximately symmetrical result about zero differential pressure. Measuring at both positive and negative voltage gives better resolution of different particles.

The charge of unknown particles (CPN200) is calibrated against a particle with a known charge (CPC200B). The maximum ratiometric (FWHM) blockade duration for each run is identified. The differential pressure at each maximum duration is recorded. The combined pressure difference of the positive and negative voltage maxima for each particle set is calculated. This equates to 2 times the pressure required to oppose electrophoretic mobility. The ratio of pressures for the various samples is proportional to the ratio of electrophoretic mobility (and therefore zeta potential). The result of these calculation steps is shown in the Table 1:

TABLE 1

| | Max Duration FWHM (ms) | Applied Pressure (cm water) | Pressure Difference +V to V (cm water) | Zeta Potential (mV) |
|---|---|---|---|---|
| CPC200B+ | 0.781 | −2 | 3.5 | −35 |
| CPC200B− | 0.935 | 1.5 | | calibration |
| CPN200+ | 1.518 | −0.5 | 1 | −10 |
| CPN200− | 1.884 | 0.5 | | calculated |

An advantage of this method is that maximum duration of the passage of a particle through a pore may be easier to identify than minimum count rate. This method may also cope better with particle populations of mixed charge.

A different embodiment of the method to determine the charge is set out below. The point where the pressure differential between the reservoirs (both due to applied pressure and gravity) is zero is of particular interest because any transport at that point is caused by the electric field alone. In cases where electrophoresis dominates electro-osmosis such that electro-osmosis is negligible, the electromagnetic interaction between the field and the charged particles is the main driving force, and the charge can be determined by recording blockade events and determining the width, for example the full width at half of the maximum value, of the blockade event. The width of the blockade event corresponds to the time it takes for the particle to traverse the pore. By comparing the width of the blockade event to a calibration particle with a known charge, the charge of the particle can be determined, i.e. if the test particle travels twice as fast as the calibration particle, then the charge of the test particle is twice as large as the charge of the calibration particle. When the second term on the right hand side of equation 1 (the term including $\zeta_{pore}$) is assumed to be small (i.e. negligible) and the third term on the right hand side of equation 1 ($Q_P/A$) is substantially zero, the flux (or the velocity of a single particle) is proportional to the charge.

When the product of inverse Debye length and particle radius is either much smaller or much larger than 1, the electrophoretic mobility and zetapotential of the particles are proportional to the surface charge density. In this case the measured event duration (e.g. FWHM of the blockade event) will be independent of particle size. In between these extremes the electrophoretic mobility becomes size-dependent. In cases where electrophoretic mobility is negatively correlated with particle size, the slope or alternatively the ratio of signal height and signal duration (e.g. FWHM) are good indicators of electrophoretic mobility.

When the externally applied pressure exactly opposes the combined pressure of not negligible electro-osmosis and inherent pressure the net pressure is zero and no fluid is flowing through the pore. At this balancing point the passage of particles through the pore is purely based on electrophoresis. This enables the measurement of electrophoretic mobility and zeta potential of particles by either analysing blockade durations or inflection (i.e. balance) point pressures.

A specific example of this method is disclosed as follows. As equipment a standard qNano system with a NP200 nanopore (100 nm to 400 nm+ sensing range) is used with buffered Potassium Chloride electrolyte (0.1M pH8). The calibration particles are CPC200B, which is "Izon Certified" carboxylated polystyrene particles produced by Bangs Laboratories and certified by Izon for size and concentration. These particles have a high negative charge in the KCl buffer. The test particles are CPN200A, which are NIST traceable (for diameter) non-functionalised polystyrene particles. These are not functionalised, so have a very low negative charge in the KCl buffer.

Figure 6:
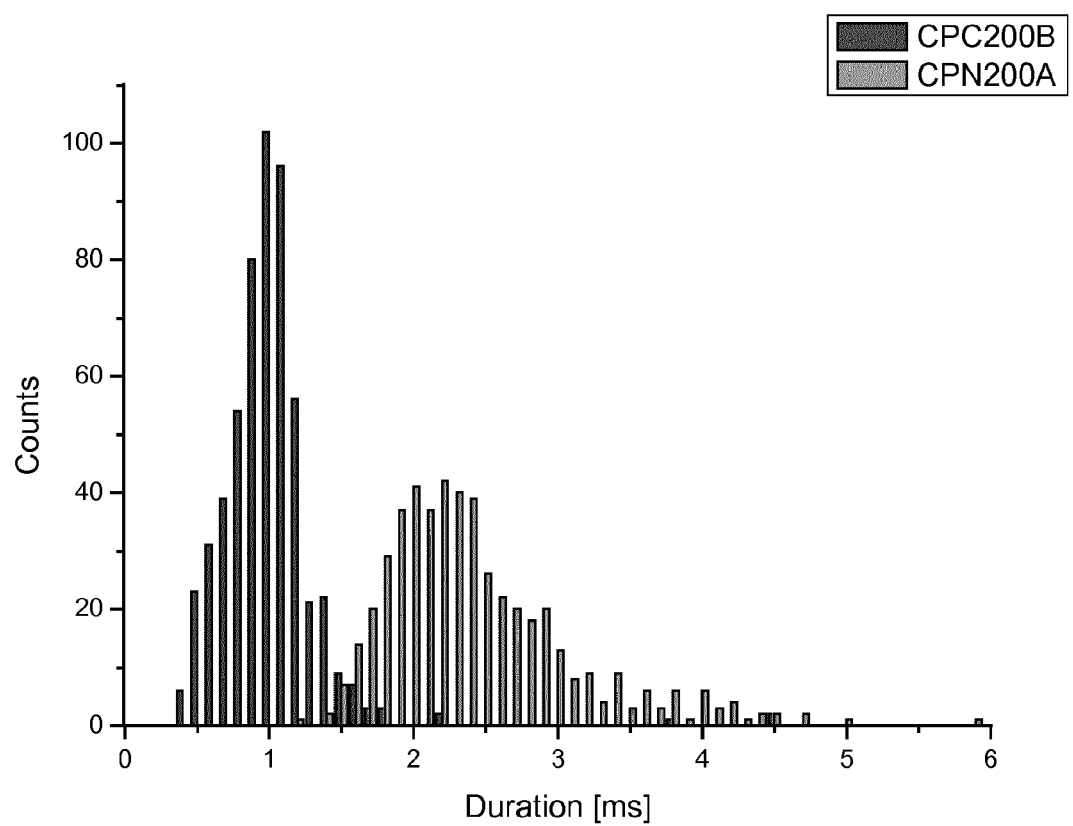
FIG. 6 is a graph showing duration of a blockade event on the horizontal axis and counts on the vertical axis.

The FWHM durations of uncarboxylated and carboxylated 200 nm polystyrene particles are compared at zero net pressure. As shown in FIG. 6, the durations of the uncarboxylated particles are significantly longer than durations measured for the carboxylated particles. This is due to the higher surface charge density of the latter.

The benefit of this method is that measurement of blockade durations at zero pressure is a measurement of a single particle as opposed to being an ensemble measurement. Hence, the duration and surface charge density of each particle can be measured. This enables charge analysis of populations with mixed charge.

A problem with calibration particles may be that the size of the calibration particles is different from the size of test particles. If the size of the calibration particles is larger than the test particles, for example, the width of the blockade event will be larger because a larger particle blocks more of the electrophoresis current than a smaller particle. To address this problem, the slope of one of the edges of a blockade event may be measured instead of the width of the event. The slope indicates the velocity of the particle. A slope of an event is independent of the size because the velocity of a particle driven by electrophoresis (and/or electro-osmosis) is independent of its size. When measuring the slope instead of the width of the blockade event, it does not matter that the size of the calibration particles may be different from the size of the test particles. Using the slope instead of the width means that calibration particles of a different size can still be useful for calibration purposes.

Figure 7:
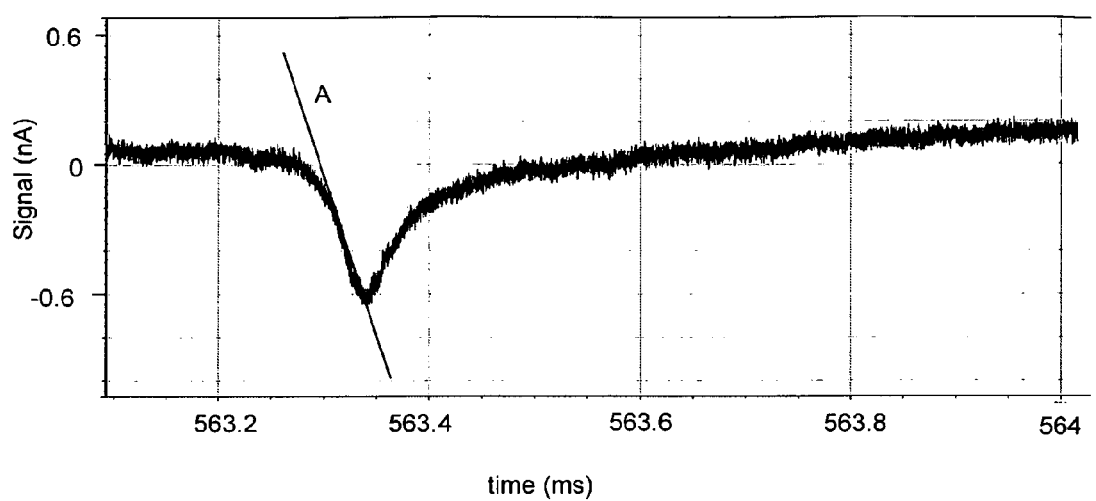
FIG. 7 is a graph showing time on the horizontal axis and measured current on the vertical axis.

The "cleanest" part of the blockade trace is the falling edge of the blockade—this edge is typically linear. FIG. 7 gives an example of a blockade event, with time delay on the horizontal axis and current on the vertical axis, and with line A indicating the falling edge of the blockade. The average velocity with which a given particle fully enters the sensing zone of the nanopore could be calculated using the gradient of this falling edge of the blockade combined with the blockade magnitude (which is the depth of the blockade with respect to the baseline average signal).

As a first approximation, the blockade magnitude divided by the FWHM duration will give an average slope for the falling edge and rising edge of the bottom half of the blockade. Better accuracy should be achieved by calculating the gradient of the falling edge alone.

In practice, it is challenging to determine the point where the pressure differential is zero, not least because it is not possible to have a pressure meter inside the pore. A pressure meter will normally be located away from the pore and the pressure will be different at that location from the pressure inside the pore.

A method to determine the point where the pressure inside the pore is zero is by monitoring the background 'baseline' signal of the electric current through the electrolyte while varying the pressure. This current method tends to work better for large pores than for small pores. There will normally always be an inherent pressure across any micro/nanopore regardless of whether the pore is oriented horizontally or vertically. This inherent pressure can be due to meniscus effects or gravity and the method disclosed herein enables determining the point of zero pressure in the pore without detailed knowledge of the inherent pressure. The configuration is such that one reservoir is at least partially filled with electrolyte without test particles, while the other (generally the top) reservoir is at least partially filled with electrolyte containing the particles that are to be tested. The conductance of the pure electrolyte is higher than the electrolyte with particles. When the pressure (due to the combination of external pressure and gravity) in the upper chamber is higher than the pressure in the lower chamber, the electrolyte with suspended particles passes through the pore.

When approaching the point of zero net pressure, the blockade frequency is near zero and the sparse blockade events are up to 100 times longer in duration than blockade events with no externally applied pressure. The minimum in blockade frequency goes hand in hand with an increase in background current. This increase is thought to be due to a combination of effects: the more conductive (particle free) electrolyte in the bottom fluid cell enters the pore; a changing pore shape; and the change in streaming potential direction.

Figure 8:
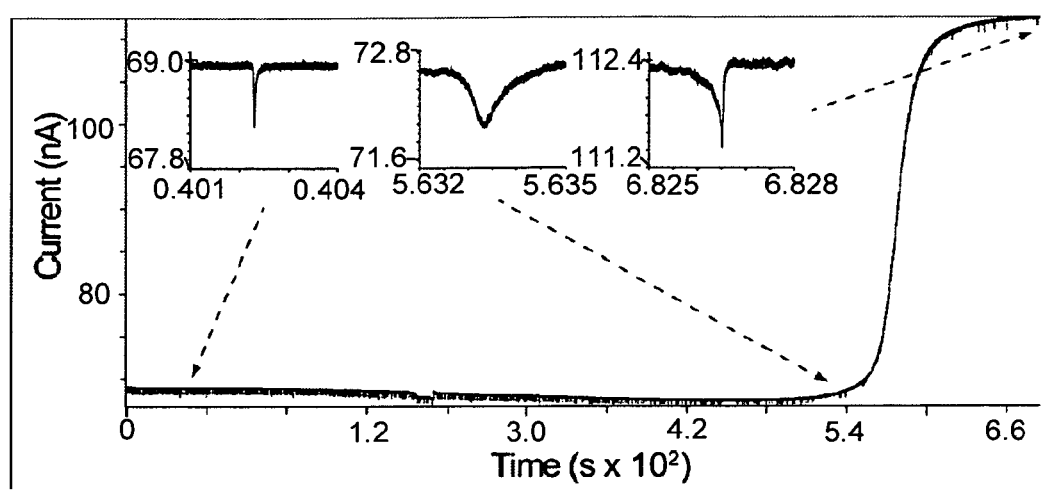
FIG. 8 is a graph showing time on the horizontal axis and measured current on the vertical axis.

FIG. 8 shows an example of the increase of the baseline signal, towards the right of the main curve. The horizontal axis shows time delay and the vertical axis shows the current through the pore. The current is mainly due to electrolyte flowing through the pore, with blockade events barely visible in the main curve. The three inserts show close-ups of the current for particular blockade events. The left insert shows a blockade event of a particle entering the pore from the narrow end of the cone of the pore and the right insert shows a blockade event for a particle entering the wide end of the pore. The event in the middle insert shows a particle entering the pore from the narrow end, but the particle moves through the pore much more slowly than in the example of the left insert because the different forces on the particle balance each other out more than for the event shown in the left insert.

Having thus found the point of zero pressure differential inside the pore by detecting the increase of the background signal, the pressure is fixed at that point and blockade events are recorded. As the pressure approaches the balance point, the blockade rate is very slow. The blockade events are now caused purely by the electric field and therefore the charge can be determined in combination with calibration data. According to a further embodiment, a large number of events may be recorded with fixed settings of the pressure and the voltage, for analysing the distribution of blockade widths. A distribution with a small variance is generally regarded as preferable over a distribution with a large variance.

An example of an application where charge measurement using a nanopore may be an important analysis tool is when analysing blood platelets. When blood platelets deteriorate over time, the surface charge of some of the platelets becomes smaller and the overall variance of the distribution of widths becomes bigger.

A second example is for quality control of paint particles. The distribution of blockade widths is preferably narrow, indicating a set of pigment particles in the paint with uniform properties, indicating in turn a high quality of paint.

Specific examples of the methods outlined above will now be discussed.

Carboxylated polystyrene particle standards with nominal diameters of approximately 200-220 nm were purchased from Bangs Laboratories and Polysciences. Uncarboxylated polystyrene particles (NIST traceable size standards) with nominal diameters of 200 nm and 4000 nm were purchased from Polysciences. The 200-220 nm particles are denoted as B121, B86, B47, PSCOOH and PS respectively, and the 4000 nm particles PS4000. The specific surface charges of B121, B86 and B47 as determined by the manufacturer were 120.8, 86, and 47 µeq/g and their nominal diameters 200 nm, 220 nm and 220 nm respectively.

Electrolyte consisting of 0.1 M KCl, 15 mM Tris buffer, 0.01% v/v Triton X-100, 3 mM EDTA, and HCl to adjust to pH8, was used in all nanopore experiments. Nanoparticles were immersed in electrolyte at concentrations of approximately $10^9$-$10^{10}$/ml.

Zetapotentials of all 200-220 nm polystyrene particles were measured on a Malvern Zetasizer Nano ZS. PALS analysis was used to determine the average zeta potential of the different nanoparticle types dispersed in Tris-buffered 0.1M KCl electrolyte. Data were obtained from 15 measurement cycles and repeated twice. The ionic strength of the dispersing media (electrolyte) was high, so the instrument selected a fast (fast field reversal mode: FFR) measurement process, in order to prolong the life of the measurement cell.

Control measurements for PSCOOH were carried out on another Malvern Zetasizer Nano ZS by a different user and also repeated twice.

Figure 9:
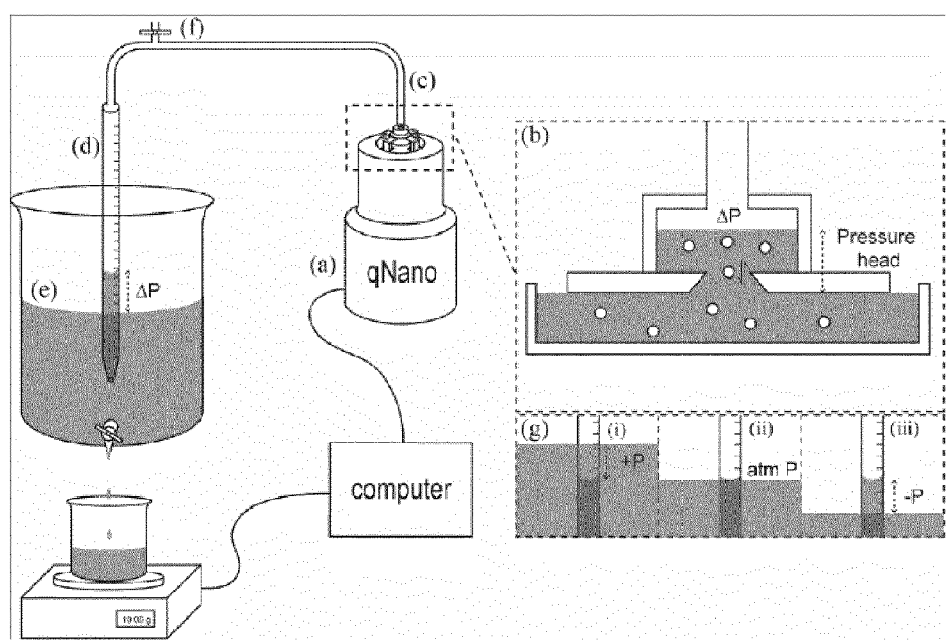
FIG. 9 is a schematic of an apparatus for electrophoresis measurements.

Tunable nanopores, which are fabricated in thermoplastic polyurethane membranes, were used in combination with IZON proprietary software to record current pulse signals. An example of a suitable nanopore and associated techniques is described e.g. in patent GB 2421303. Briefly, a flexible polyurethane membrane containing a single conical nanopore was placed between top and bottom fluid cells, each containing a measurement electrode, as shown in FIG. 9 (b). By applying a constant potential across the pore (typically less than 1 V) the translocation of particles through the pore can be detected as a brief change in the background current. Changing the distance between the geared jaws connected to the four arms of the membrane, the geometry of the pore can be tuned in real time to better suit different particle sizes. The dimensions of the pore openings and membrane thickness were determined using SEM and a digital micrometer respectively. Experiments using 4 µm particles (PS 4000) were conducted at a voltage of 0.02 V with particles only in the top fluid cell, whilst measurements for 200-220 nm polystyrene particles were carried out at a voltage of 0.3 V with equal concentration of particles in both fluid cells.

FIG. 9 shows a schematic of the variable pressure set up used with the qNano pore sensor (a). Pressure in the top fluid cell (b) is precisely controlled via a flexible tubing connection (c) by varying the height difference between the water level in a partially submerged burette (d) and the water level of a large water reservoir (e). The burette was equilibrated with atmospheric pressure by opening a valve (f). Progression of an experiment where pressure is varied from positive to negative is shown in (g).

The pressure applied across the membrane was precisely regulated by a manometer arrangement (FIG. 9). In a typical experiment the valve (FIG. 9(f)) was closed, sealing the burette and tubing, following equilibration of the fluid cell with atmospheric pressure. In this state, the pressure across the pore was that of the gravitational pressure head (FIG. 9(b)). The pressure in the top fluid cell was then reduced by gradually releasing water at a constant flow rate from the beaker, so that the height of fluid in the burette was greater than that in the beaker, with the difference in heights creating an applied pressure. Applied pressures were known precisely, because the weight of fluid displaced for a given change in height of the water in the main beaker relative to that in the burette was calibrated. Due to the lowering of the water level in the beaker, the rate at which the fluid is displaced decreases slowly with time. This small deviation from the linear relationship between pressure and time was considered when calibrating the system. The units of pressure used refer to the equivalent height of water.

Electro-osmotic flow measurements were made using the current monitoring method. Rectangular micro channels (dimensions 0.022×0.1×30 mm) joining 2 mm diameter wells were fabricated from the same thermoplastic polyurethane used to make tuneable elastomeric nanopores (Ellastollan 1160, BASF) by hot embossing. Channels were initially filled with electrolyte to replicate the pore sensing experiments (Tris-buffered 100 mM KCl, adjusted to pH 8 by adding conc. HCl). With 500 V applied via platinum electrodes and a steady current established, the electrolyte in one well was replaced with electrolyte at a slightly lower concentration (98 mM). Electro-osmotic flow rates were measured by monitoring the linear current change as the high concentration electrolyte was displaced. Channels were wetted with methanol and washed with deionised water before and after each measurement.

The results of the measurements and calculations are now discussed. We use measurements of blockade rate to derive the zeta potential of nanoparticles using equation 1 above. Calculation of zeta potential is achieved by setting J=0 in equation 1, so that the applied pressure exactly opposes the combined effect of electro-osmosis, electrophoresis and inherent pressure. Use of equation 1 requires measurement of $\zeta_{pore}$, and determination of the inherent pressure head. Of the other terms, $\epsilon$ and $\eta$ are known under standard laboratory conditions, while $Q_P$, A and E were calculated using a conical profile based on SEM imaging of the pore under the same stretch conditions used in the experiments. Effective radii s and l of the small and large pore openings were used to calculate the electric field, while hydrodynamic radii $s_h$ and $l_h$ were used to derive pressure variation. Effective radii were calculated, such that the area of circles of radii s and l is the same as the actual area of the openings, whilst hydrodynamic radii were determined by dividing area by half the pore perimeter. The pore wall zeta potential was determined by measuring electro-osmosis in a well-defined channel (see experimental section).

The electric field within the pore was calculated by deriving the pore resistance, including access resistance between the pore openings and the electrodes, $$E_z(z) = -I_0 \frac{dR}{dz} = \frac{V_0}{R_0}\left(\frac{\rho}{\pi\lambda(z)^2}\right) \quad (2)$$

where for a conical pore $$\lambda(z) = l - \frac{l-s}{d}z$$

And $$R_0 = \frac{\rho(d + 0.8(s+l))}{\pi s l}.$$

$E_z$, $I_0$, $V_0$, $\rho$, and $R_0$ are the electric field component along the pore axis, electric current, voltage, resistivity of the electrolyte and resistance of the electrolyte filled pore respectively.

The pressure-driven volumetric flow rate $Q_P$ is calculated by considering the flow resistance through the pore. The contribution beyond the membrane surfaces is taken to be half the pressure drop across a thin circular orifice. The same assumption contributes negligible error to the pressure drop between a half space and the end of a cylindrical tube of finite or infinite length.

$$P = P_{in} + P_{ends} \quad (3)$$

$$= Q_P \left( \int_0^d \frac{8\eta}{\pi\lambda(z)^4} dz + 1.5\eta\left(\frac{1}{s_h^3} + \frac{1}{l_h^3}\right)\right)$$

$$= Q_P \left( \frac{8\eta d\left(\frac{1}{s_h^3} - \frac{1}{l_h^3}\right)}{3\pi(l_h - s_h)} + 1.5\eta\left(\frac{1}{s_h^3} + \frac{1}{l_h^3}\right)\right)$$

Calculations of both E and $Q_P$ assume that transport is dominated by the vector component parallel to the pore axis z, which is appropriate for a pore with width that varies slowly with length, as is the case for the tuneable elastomeric nanopores used in this study.

The experiment is carried out in a high-salt regime, where the Debye length does not exceed 3 nm, so electro-osmotic transport is described by plug flow. The velocity of the electro-osmotic flow can be calculated by applying the Helmholtz-Smoluchowski equation:

$$v_{eo} = -\epsilon \zeta_{pore} E/\eta \quad (4)$$

The description of electro-osmotic flow rate through the conical nanopore assumes that the electro-osmotic velocity $v_{eo}$ is proportional to the local electric field E, an appropriate assumption for present channels and 0.1 M KCl electrolyte.

Zeta potentials of pore walls were calculated by evaluating electro-osmotic flow within microchannels and using equation 4. A value of $\zeta_{pore}=-8\pm3$ mV was obtained for the specific electrolyte (Tris-buffered 0.1 M KCl) and elastomeric material used in nanopore experiments. Uncertainty in the quoted value (37.5%) is based on numerous measurements using different channels of the same material. The pressure which produces an equivalent volumetric flow rate to the electro-osmotic flow (denoted as electro-osmotic pressure) was calculated to be $4.4\pm2.8$ mm $H_2O$ (using equations 2, 3, 4 and considering that the fluid flow due to electro-osmosis is $\pi s_h^2 v_{eo}$).

The inherent pressure across the pore is the pressure due to gravitational head and meniscus effects when the system is equilibrated with atmospheric pressure, so that no pressure is externally applied via the variable pressure system (FIG. 9(g)(ii)). We make a clear distinction between inherent pressure and externally applied pressure, which is due to height difference of water levels in the burette and the beaker (FIG. 9(g)). The sum of both is denoted as 'net pressure' which gives rise to the total volumetric flow rate $Q_P$. A precise knowledge of inherent pressure is important for measurement of the zeta potential, particularly in vertical fluid cell arrangements, where the inherent pressure can be significant.

The inherent pressure in the top fluid cell was determined using the variable pressure method described above. In this case, a large pore (small pore opening diameter of approximately 10 µm) was used with 4 µm uncarboxylated polystyrene particles (diluted to 0.1 wt % in Tris-buffered 0.1 M KCl), to ensure that particle transport was dominated by pressure, i.e. electrokinetic forces were negligible. The inherent pressure was measured by increasing the negative pressure until particle translocations stopped. A trace from one of the replicates of this experiment is presented in FIG. 8. The insets depict representative single particle blockade events at different times during the experiment, all displayed over a 0.3 s time interval. As the pressure in the top fluid cell was reduced, thereby reducing average particle velocity, the duration times of blockade events increased. When the net pressure in the top fluid cell became negative, fluid and particles began to flow from the bottom to the top fluid cell. This change in particle flow direction is indicated by a change in the shape of the blockade event, which is a result of the resistance gradient in the pore due to its conical shape. When approaching the point of zero net pressure, the blockade frequency is near zero and the sparse blockade events are up to 100 times longer in duration than blockade events with no externally applied pressure. The minimum in blockade frequency goes hand in hand with an increase in background current. This increase is possibly due to a combination of effects: the more conductive (particle free) electrolyte in the bottom fluid cell enters the pore; a changing pore shape; and the change in streaming potential direction.

FIG. 8 is a representative trace from an approximately 11 min long variable pressure experiment used to determine the inherent pressure head in the top fluid cell. From left to right the insets show single particle pulse traces initially travelling from the small to large pore openings when the pressure head is large, slowing as the net pressure approaches zero, and then the direction of the particle translocation reversing as the net pressure becomes negative in the top fluid cell.

The pressure in the top fluid cell for a 40 µL sample was measured at 4.7 mm±0.3 mm $H_2O$.

Previous studies of nanoparticle surface charge using nanopores have not accounted for inherent pressure. Although this pressure is relatively small, it can overcome electrophoretic forces on nanoparticles which carry a low surface charge, and can play a significant role in both horizontal and vertical sample cell arrangements. Fluid flow rates through nanopores are negligible, so pressure differences across a pore do not equalise over practical time scales. Therefore, the pressure difference between both sample cells needs to be either measured or equalised to enable an accurate measurement of particle zeta potential. Having determined the inherent pressure in the fluid cell, it was possible to accurately measure the electrokinetic forces on nanoparticles using the variable pressure method with smaller pores.

FIG. 4 shows S-curves (i.e. cumulative counts versus applied pressure) for various polystyrene particles, acquired using the variable pressure method fitted with cubic (PS, B47, B86, B121) and parabolic (PSCOOH) curves. Externally applied pressure is given in cm H2O.

FIG. 4 shows the cumulative counts versus applied pressure for a range of 200 nm polystyrene particles (PS, B47, B86, B121, and PSCOOH). When applied pressure is gradually varied from atmospheric to negative pressure (see FIG. 9(g)), the cumulative counts describe an S-curve for each particle type. Since blockade frequency (counts/time) scales linearly with pressure, the two halves of the S-curves are expected to be parabolic, with one branch having negative and the other positive curvature. The parabolic dependency of accumulated counts on pressure is demonstrated in equation 5 with P being the applied pressure, and a, b and c being constants which depend on particle type and concentration.

$$\text{Counts} = a + b*P + c*P^2 \tag{5}$$

$$BF = \frac{d(\text{Counts})}{dt} = (b + 2c*P)*\frac{dP}{dt}$$

The pressure at the inflection point (i.e. the point where the curvature of the graph changes sign) of each S-curve allows calculation of the particle electrokinetic surface charge. The gradient is expected to be zero at this inflection point. However, peculiarities such as non-through and multiple blockade events (FIG. 10 a, b) result in a non-zero blockade frequency. Hence, the inflection points of S-curves were initially determined using 3rd-order polynomial fits to the experimental data. Both branches of the S-curve were then fitted with parabolas, omitting the data within P=0.5 cm $H_2O$ of the initial inflection point (see fit to PSCOOH in FIG. 4). This approach was sufficient to exclude all atypical events. From the parabolic fits, the inflection point pressures for the different particle types were equal to $-b/2c$ (equation 5). Averaging triplicate measurements, the calculated externally applied pressures at the inflection point were $0.77\pm0.08$ cm $H_2O$, $1.35\pm0.09$ cm $H_2O$, $1.58\pm0.10$ cm $H_2O$, $2.17\pm0.24$ cm $H_2O$, and $1.35\pm0.12$ cm $H_2O$ for PS, B47, B86, B121 and PSCOOH respectively. Inflection point pressures are independent of particle concentration, since b and c scale linearly with concentration.

Figure 10:
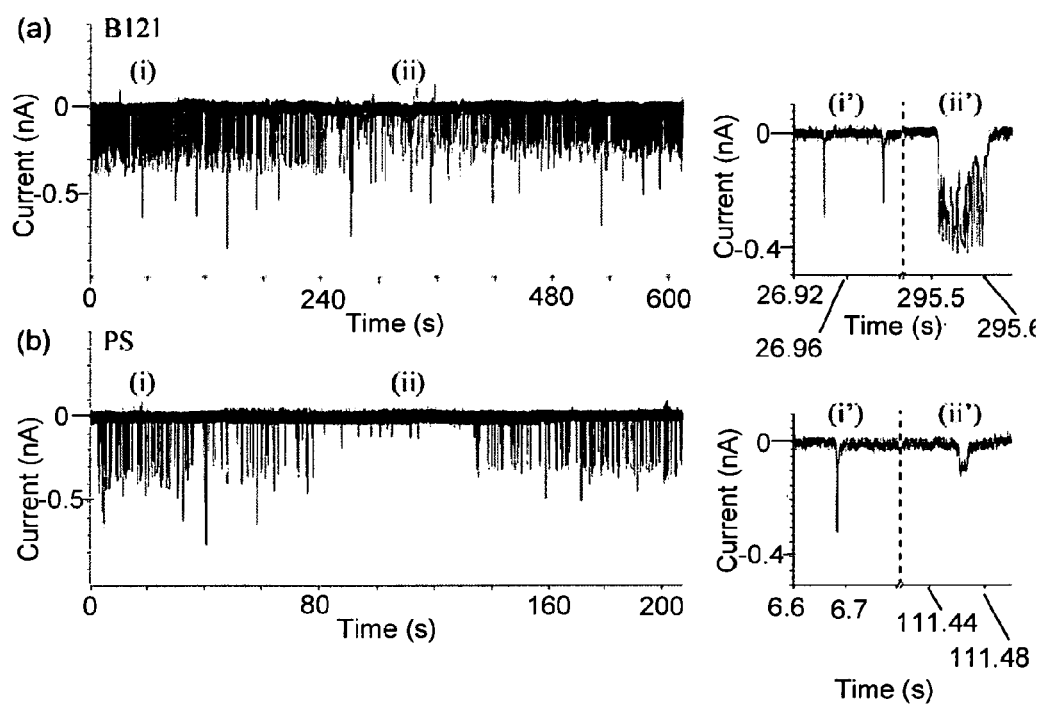
FIG. 10 shows four graphs showing time on the horizontal axis and measured current on the vertical axis.

FIG. 10 shows traces from high surface charge B121 (a) and low surface charge PS (b) variable pressure experiments. The current baseline is shifted to 0 nA to remove baseline drift and for simplified event analysis. Insets show blockade events at different times in the pressure titration experiments. (a)(i') and (b)(i') show regular blockade events for both the high and low charged particle types under pressure. (a)(ii') and (b)(ii') show representative blockade events for the particles when the pressure across the pore approaches zero.

Interestingly, along with longer duration times, blockade events close to the inflection point typically had very low magnitudes (FIG. 10(b)(ii')). Low magnitude signals are thought to be due to particles entering the pore, but not traversing it. These events could be due to Brownian motion, which plays a significant role in the movement of low charge particles. For B121 particles, both low magnitude events and multiple events are observed. Multiple events are thought to be due to particles being trapped in the pore constriction for up to 40 ms, while moving backwards and forwards. The example in FIG. 10(a)(ii') shows a particle apparently entering the pore and becoming trapped, before translocating under electrokinetic forces.

FIG. 11 shows that, for a variety of polystyrene particles, the relationship between the inflection point pressure and surface charge density is approximately linear. This linear dependence is expected, because the zeta potential of nanoparticles scales linearly with surface charge density. Surface charge densities were calculated by converting the specific charges 121, 86 and 47 µeq/g of B121, B86 and B47 respectively (as given by Bangs Laboratories using acid/base titration) into C/nm2 through multiplication by the Faraday constant. Weight was converted into surface area by considering nominal particle radii and assuming a density of polystyrene of 1.06 g/cm3. Calculated surface charge densities correspond to surface areas per carboxylate group of 0.39 nm2, 0.50 nm2 and 0.91 nm2 for B47, B86, and B121 respectively. Uncarboxylated PS particles have an unknown, non-zero surface charge due to sulphate surface functionality.

In FIG. 11, dependence of the inflection point pressure (cm H2O) on surface charge density for particles B47, B86 and B121 is fitted by a straight line. Non-zero surface charge of uncarboxylated PS particles is indicated by the arrow. The dashed horizontal line at −0.03 cm H2O is the sum of electro-osmotic transport and inherent pressure.

The sum of electro-osmotic and inherent pressure (dashed line in FIG. 11) is subtracted from the inflection point pressure to obtain the total pressure ('total inflection pressure') required to oppose electrophoresis and extract the zeta potential of the polystyrene particles. It is expected that the total inflection pressure required to oppose electrophoresis scales with the inverse of blockade duration. Therefore, the product of duration and total inflection pressure for various particle types should be constant. In Table 2, pressures are compared with the blockade durations extracted near the point where applied pressure is equal to the sum of inherent and electro-osmotic pressures, so that electrophoresis is the sole significant driving force of particles through the pore. For traces displayed in FIG. 10 this equilibrium point was reached after approximately 5 s. Blockades in the first 10-12 s of each run were evaluated and full width half maximum (FWHM) durations extracted. The durations of at least 45 blockades were averaged for each sample. The final column of Table 2 shows a reasonably constant value.

In Table 2, for different particle types, the mean FWHM duration for events with dominant electrophoresis is listed, along with inflection pressures, and the product of these two measures. Numbers in brackets represent the standard deviation.

TABLE 2

| Sample | FWHM [ms] | Inflection Pressures [cm H$_2$O] | FWHM * Pressure [ms * cm] |
|---|---|---|---|
| B121 | 0.213 (0.041) | 2.14 (0.24) | 0.46 (0.14) |
| B86 | 0.264 (0.070) | 1.55 (0.10) | 0.41 (0.13) |
| B47 | 0.282 (0.048) | 1.32 (0.09) | 0.37 (0.09) |
| PSCOOH | 0.298 (0.052) | 1.32 (0.09) | 0.39 (0.10) |
| PS | 0.622 (0.128) | 0.74 (0.08) | 0.46 (0.14) |

The tuneable elastomeric nanopores used in our experiments have been previously characterised, and are conical in shape. From analysis of the SEM images, s, l, $s_h$ and $l_h$ were 15.3±2.3, 470±70, 13.6±2.0 µm and 460±70 nm respectively. The membrane thickness d at the strain used was 220±15 µm.

Having determined the zeta potential of the pore, the inherent pressure, and the applied pressure required to minimise the event rate, we used the Nernst-Planck equation (equation 1) and a simple geometric model, customised for these pores (equations 2 and 3), to derive the particle zeta potential of the particles (Table 3). The quoted error of $\zeta$ is dominated by uncertainty in the geometric dimensions of the pore, since pressure-driven flow is highly dependent on pore geometry. As a first approximation, this calculation depends on the cube of the effective radius, so the percentage error is three times the measurement uncertainty in the pore opening radii. The zeta potentials measured using PALS are very similar to those obtained from the variable pressure method (Table 3). The variable pressure method suggests that surface charge increases in the sequence PS, PSCOOH, B47, B86, then B121. In contrast, PALS suggests a different order of increasing charge, being PS, B47, B121, B86 then PSCOOH. Titration results provided by Bangs for B47, B86 and B121 (Table 3) support the results obtained using the variable pressure method. In Table 3, a comparison of zeta potentials measured using the variable pressure method, PALS, and surface charge densities determined by acid/base titration are shown. Numbers in brackets represent the measurement uncertainty.

TABLE 3

| Sample | $\zeta_{particle}$ (Var. Pressure) [mV] | $\zeta_{particle}$ (PALS) [mV]* | Surface Charge Density (C/nm2) |
|---|---|---|---|
| B121 | −39 (13) | −26.7 | −4.09 |
| B86 | −28 (9) | −26.8 | −3.20 |
| B47 | −24 (8) | −23.0 | −1.75 |
| PSCOOH | −24 (8) | −27.8 | —** |
| PS | −13 (5) | −17.4 | —** |

*Zeta potentials were averaged over two measurements and repeats agreed to within 3%. Control measurements for PSCOOH on another zetasizer instrument were −29.7 mV, within 7% of the recorded values.
**not provided by the manufacturer.

It will be appreciated by the person of skill in the art that various modifications may be made to the above described embodiments without departing from the scope of the present invention.

For example, the techniques disclosed herein whereby the electric current is measured and whereby the potential difference between the chambers is kept constant may be modified such that the potential difference is measured and the electric current is kept constant. Other details of these techniques may need to be modified as appropriate.

The potential difference between the chambers in the described embodiments is generally kept constant while the pressure is varied, but in a modification of these embodiments the potential difference may also be varied while keeping the pressure difference constant, or both the potential difference and the pressure difference may be varied. Again, other details may need to be modified accordingly.

The invention claimed is:

1. A method of determining the charge of at least one test particle, comprising:
    applying one of an electric current or a voltage across an aperture connecting two chambers, whereby the chambers are at least partially filled with electrolyte and whereby the at least one test particle is suspended in the electrolyte of at least one of the chambers;
    measuring the other of the electric current or voltage across the aperture;
    varying a pressure differential between the two chambers, wherein the pressure differential is a non-zero pressure differential;
    determining the charge based on the measurements of the electric current or voltage;
    determining a balance pressure differential at which the force on the at least one test particle due to the pressure differential is equal and opposite to the force due to the voltage across the aperture; and
    wherein the balance pressure differential is determined by extrapolating the linear relationship between pressure differential and a transport rate of the at least one test particle to determine the pressure differential where the transport rate is zero.

2. The method according to claim 1, further comprising correcting the pressure differential for the gravitational force on the at least one particle and/or for the force on the at least one particle due to a meniscus in at least one of said chambers and/or the force on the at least one particle due to electro-osmosis.

3. The method according to claim 1, further comprising determining the time required for a particle to traverse the aperture in dependence on the pressure differential so as to estimate the pressure differential where the transport rate is zero.

4. The method according to claim 1, further comprising using at least one calibration particle with a known charge for calibrating the quantitative relationship between the charge of the at least one particle and the pressure differential.

5. The method according to claim 4, wherein calibrating said quantitative relationship comprises calibrating said quantitative relationship where the transport rate is zero.

6. The method of claim 1, further comprising setting the pressure differential between the chambers to zero such that transport of the at least one particle is only driven by electrophoresis.

7. The method according to claim 6, further comprising determining the time required for a particle to traverse the aperture in dependence on the voltage so as to estimate the charge of the particle.

8. The method according to claim 6, further comprising estimating when the pressure differential between the chambers is zero, based on a measurement of a background current in the electrolyte in dependence on the pressure differential.

* * * * *